US00PP17976P2

(12) United States Plant Patent
Sizemore et al.

(10) Patent No.: US PP17,976 P2
(45) Date of Patent: Sep. 4, 2007

(54) SWEETPOTATO PLANT NAMED 'STOKES PURPLE'

(50) Latin Name: *Ipomoea batatas*
Varietal Denomination: Stokes purple

(76) Inventors: Michael E. Sizemore, 1124 Wall Loop Rd., Walnut Cove, NC (US) 27052; Russel L. Slate, 1871 N. Stokes School Rd., Danbury, NC (US) 27106; David A. Priddy, Jr., 3838 NC 8 Highway, S., Walnut Cove, NC (US) 27052

( * ) Notice: Subject to any disclaimer, the term of this patent is extended or adjusted under 35 U.S.C. 154(b) by 73 days.

(21) Appl. No.: 11/243,608

(22) Filed: Oct. 5, 2005

(51) Int. Cl.
*A01H 5/00* (2006.01)

(52) U.S. Cl. ..... Plt./258
(58) Field of Classification Search ..... Plt./258
See application file for complete search history.

(56) References Cited

U.S. PATENT DOCUMENTS

PP14,912 P3 6/2004 Pecota et al. ..... Plt./258
PP15,028 P3 7/2004 Pecota et al. ..... Plt./258
PP15,038 P3 7/2004 La Bonte et al. ..... Plt./258
PP15,056 P3 8/2004 Pecota et al. ..... Plt./258
PP15,380 P3 11/2004 LaBonte et al. ..... Plt./258
PP15,437 P3 12/2004 Pecota et al. ..... Plt./258

OTHER PUBLICATIONS

Irradiation Replaces Methyl Bromide for Sweetpotato Exported from Hawaii; Peter A. Follett, USDA–ARS, Pacific Basin Agricultural Research Center, Hilo, Hawaii (MS PowerPoint Presentation, pp. 1–21).
Approval of Irradiated Sweet Potatoes Has Critics Steamed, The Washington Post, Mar. 9, 2004 by Cindy Skrzycki, pp. 1–3.
REVIEW Physiological Functionality of Purple–Fleshed Sweet Potatoes Containing Anthocyanins and Their Utilization in Foods, Iku Suda, Tomoyuki Oki, Mami Masuda, Mio Kobayashi, Yoichi Nishiba and Su Furuta, Received Oct. 30, 2002; accepted May 28, 2003 pp. 167–173.
Select Markets for Taro, Sweet Potato and Yam, A report for the Rural Industries Research and Development Corporation, compiled by Grant vinning, Asian Markets Research, May 2003 (pp. ix, 3–32).

*Primary Examiner*—Anne Marie Grunberg
*Assistant Examiner*—Annette H Para
(74) *Attorney, Agent, or Firm*—MacCord Mason PLLC

(57) ABSTRACT

A new and distinct variety of *Ipomoea batatas* called 'Stokes purple' is shown and described. The plant is a prostrate vine, producing several branching vines off the main vine with tri-lobed leaves. The 'Stokes purple' plant is distinguished by its storage root, which has purple flesh and purple skin.

4 Drawing Sheets

Genus and species name: The present invention relates to a new and distinct sweetpotato variety of *Ipomoea batatas*.

Variety denomination: This new and distinct sweetpotato variety is identified as 'Stokes purple'.

BACKGROUND OF THE INVENTION

Sweetpotatoes (*Ipomoea batatas*) are a perennial herbaceous dicotyledonous species of the morning glory family Convolvulaceae. Sweetpotatoes, unlike the Irish potatoes (*Solanum tuberosum*), are not a tuber propagated plants. A "tuber" is a short, thickened portion of an underground branch. Along a tuber are found "eyes," each of which comprises a ridge bearing a scale-like leaf (analogous to a branch leaf) having minute meristematic buds in the axial of the leaf. By contrast, sweetpotato roots are developmentally and anatomically true roots, lacking meristematic buds, and are not derived from an underground branch. Sweetpotatoes do not form tubers.

Sweetpotato plants produce primary fibrous roots, pencil roots and storage roots. Storage roots are attached to the stem by a stalk of thinner root that is usually initiated at the stem node just below the soil line. Skin color of storage roots typically ranges from white to brown to red-orange. Flesh color of storage roots is typically red-orange, orange, yellow or white. The flesh can be either soft or firm.

A few sweetpotato varieties produce storage roots with purple flesh, or purple skin, or both purple flesh and purple skin. These varieties may be desirable for any combination of their salability, unique flavor or nutritional benefit. These varieties produce various anthocyanins, which cause the purple color. Anthocyanins have attracted attention because they have multiple physiological properties, including radical-scavenging (or antioxidative), anti-mutagenic, hepato-protective, antihypertensive, and antihyperglycemic properties. Because of these beneficial properties, the more anthocyanins, or the greater the variety of anthocyanins, that can be produced in the storage root, the better.

One way to gauge the extent or the variety of anthocyanins is to look for stability of the purple color after heat stress, e.g. cooking. The degree of color stability after heating is correlated with the number of anthocyanin species.

It is thus desirable to produce a larger variety of sweetpotato with purple flesh and purple skin. It is further desirable to produce a variety of sweetpotato with purple flesh and purple skin that has the ability to grow in the southeastern United States. It is further desirable to produce a sweetpotato with purple flesh, which maintains its purple color after heat stress.

SUMMARY OF THE INVENTION

This new and distinct sweetpotato variety is identified as 'Stokes purple', and is distinguished from all other varieties of *Ipomoea batatas* known to the inventors by its large storage roots having deep purple skin and deep purple flesh. It is also distinguished because it is the only purple-fleshed, purple-skinned sweetpotato known to the inventors able to grow in the Southeastern United States. The inventors are aware that others in Southeastern United States have, however, been able to grow plants producing white-skinned, purple-fleshed storage roots. It is further distinguished based on its ability to maintain its purple color after cooking.

Lineage: The parentage of the 'Stokes purple' plant is unknown. One of the inventors was given a purple-skinned, purple-fleshed sweetpotato storage root of unknown origin. From this single root, slips were produced. These slips were used to produce plants. After approximately three growing seasons, the inventors discovered the unique characteristics of the 'Stokes purple' during outdoor cultivation in Stokes Co., North Carolina. (USDA Zone 7A (0° F. –5° F.).

Asexual Reproduction: The 'Stokes purple' has been asexually reproduced using vegetative cuttings by the inventors in Stokes County, N.C. The 'Stokes purple' has also been asexually reproduced, for the inventors, through micropropagation. Asexual production of the 'Stokes purple', by the inventors, has shown that the unique features of this sweetpotato are stable and the plant reproduces true to type in successive generations of asexual propagation.

SUMMARY OF THE INVENTION

*Ipomoea batatas* 'Stokes purple' is a prostrate vine, producing several branching vines off the main vine. The 'Stokes purple' plant is approximately 20 cm high and 91 cm wide at three months. The storage roots produced by the 'Stokes purple' are distinguished from all other *Ipomoea batatas* known to the inventors based on their purple skin, purple flesh, and large size. The 'Stokes purple' is also distinguished based on its ability to grow in the Southeastern United States. The 'Stokes purple' is further distinguished by its production of a purple-fleshed storage root which is able to maintain its purple color after cooking.

BRIEF DESCRIPTION OF ILLUSTRATIONS

The file of this patent contains at least one photograph executed in color. Copies of this patent or patent application publication with color drawings(s) will be provided by the office upon request and payment of the necessary fee.

BOTANICAL DESCRIPTION OF THE PLANT

Figure 1:
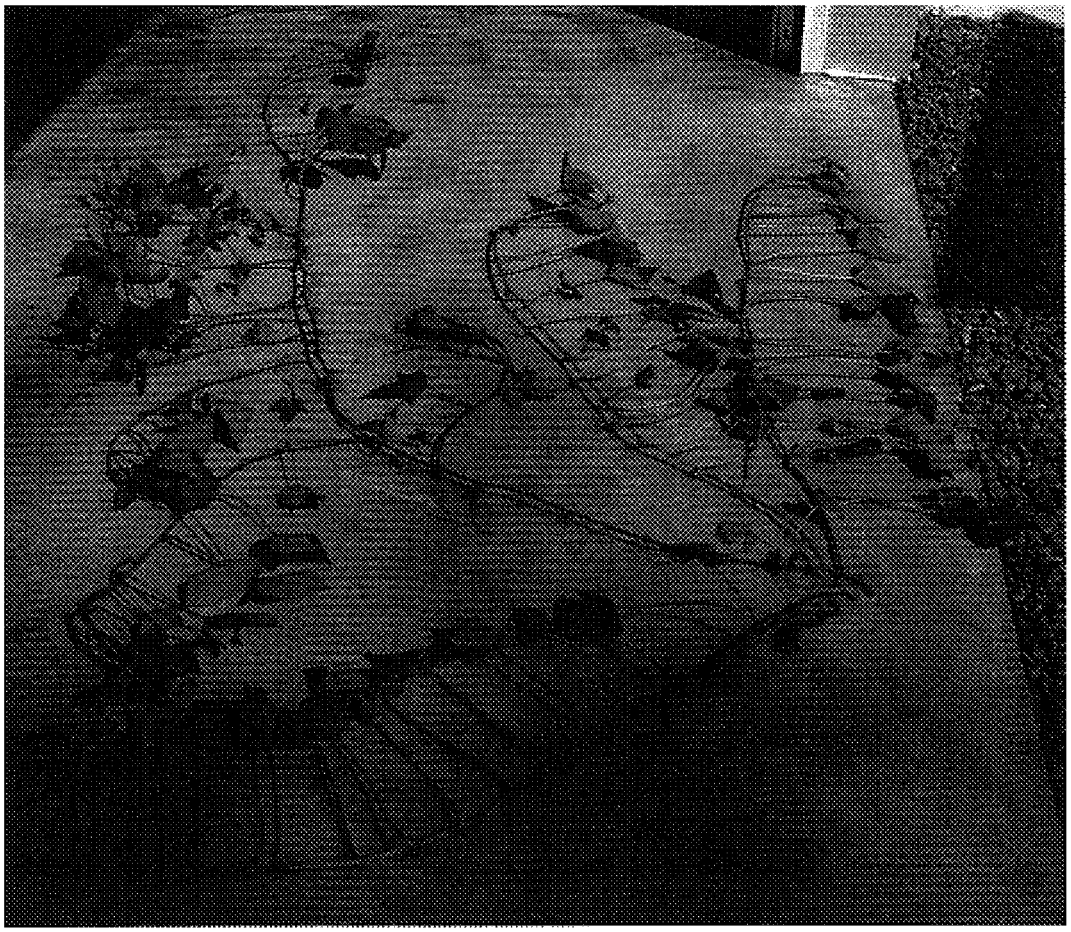
FIG. 1 is a photograph of the above-ground biomass of the novel variety of sweetpotato identified as 'Stokes purple'.
Figure 2:
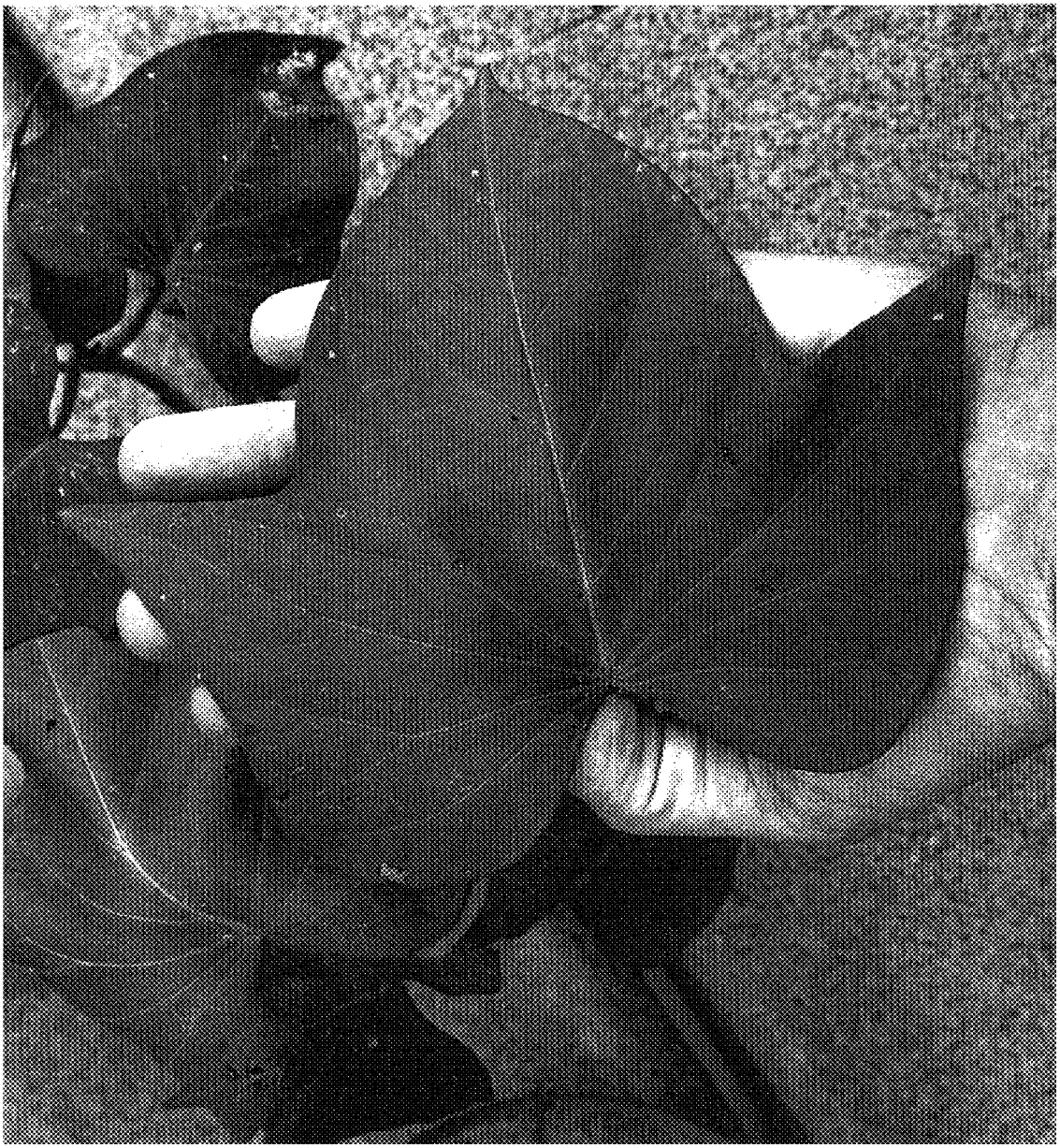
FIG. 2 is a close-up photograph of a mature leaf of the 'Stokes purple' plant.
Figure 3:
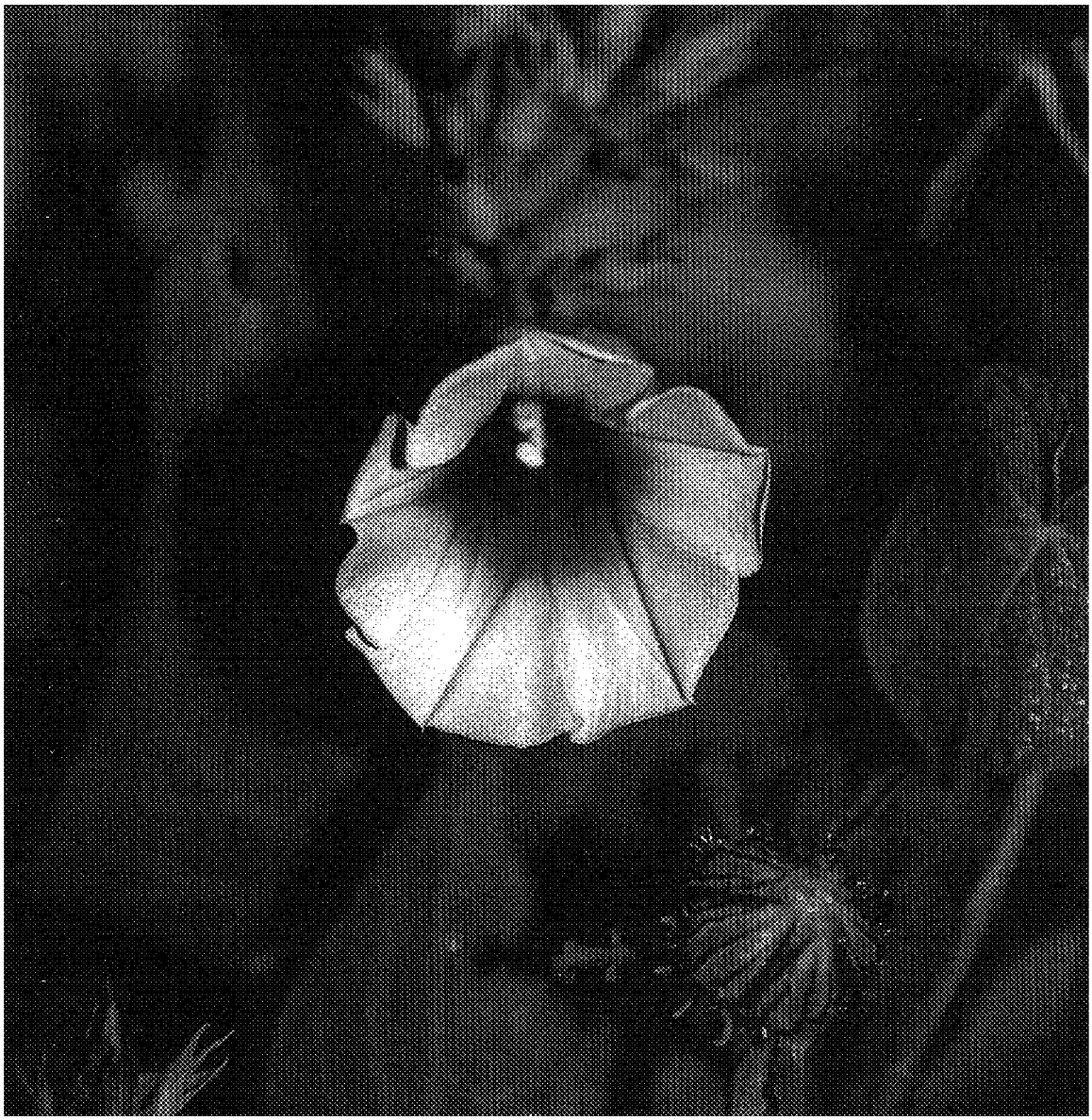
FIG. 3 is a photograph of a flower from the 'Stokes purple' plant.
Figure 4:
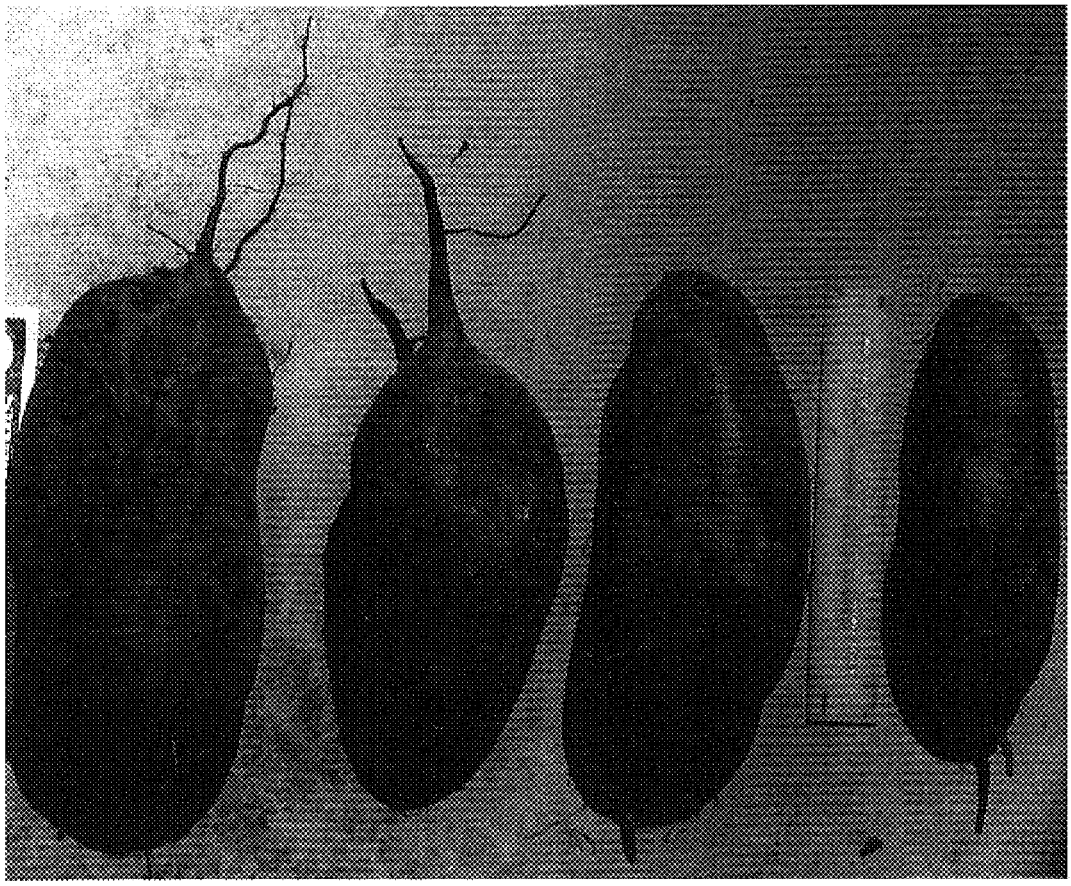
FIG. 4 is a photograph of a storage root from the 'Stokes purple'.

A detailed description of the *Ipomoea batatas* 'Stokes purple' follows. Colors are based on The Royal Horticultural Colour Chart (1986). All measurements, with the exception of storage root measurements and Royal Horticultural Colour Chart comparisons, were taken from a representative 3 month old plant grown outdoors in Stokes Co., North Carolina. (USDA Zone 7A (0° F.–5° F.). Storage root measurements are an average of the measurements of four storage roots, selected to represent variability, harvested in early September 2005. Color comparisons were based on a representative, approximately 3 month old plant grown in glass house conditions in Nash Co., North Carolina.

Classification:
- *Botanical.*—*Ipomoea batatas* 'Stokes purple'.
- *Parentage.*—Unknown.
- *Propagation.*—Vegetative cuttings.

Plant:
- *Size.*—20 cm high, 91 cm wide at 3 months.
- *Habit.*—Prostrate with 1 main vine growing up from stem.
- *Branching.*—7 branches per plant.

Leaf:
- *Shape.*—Tri-lobed.
- *Base.*—Cordate.
- *Apex.*—Acute.
- *Size.*—Length 15.4 cm, width 16 cm.
- *Arrangement.*—Single stem every 8 cm. apart.
- *Margin.*—Entire.
- *Texture/substances.*—Smooth.
- *Petioles.*—Length 15.6 cm.
- *Mature leaf color.*—Upper surface: 147A: lower surface: 147B.

Main stem:
- *Length.*—1 cm.
- *Thickness.*—0.8 cm.
- *Color.*—Young stem: 146B; mature stem: 148A.
- *Hardiness.*—USDA Zone 7A (0° F.–5° F.).
- *Vigor.*—Approximately 33 percent faster than other sweetpotato plants.

Vine:
- *Length.*—243 cm.
- *Thickness.*—0.8 cm.
- *Internode length.*—5.5 cm (average for plant).
- *Color.*—135B.

Inflorescence:
- *Bloom period.*—60 days (approx.).
- *Flower arrangement.*—Generally a cyme.
- *Floral symmetry.*—Radial symmetry with five fused petals.
- *Floral buds.*—0.2 cm long at 14 days before opening.
- *Floral size.*—Corolla length, 4 cm. Corolla width, 4.5 cm.
- *Floral color.*—Petal color changes from the throat to the distal portion as follows: 83A (approximate inner third of petal); 80A (approximately middle third of pedal); 69B (approximate outer third of petal).
- *Stigma.*—Number, 1. Length, 3 mm. Color, 155B.
- *Stamen.*—Number, 6. Length 1.5 cm (average). Color, Anther: 18D; Filament: 155B.
- *Floral buds.*—2 cm at 14 days before opening.
- *Peduncle.*—Length, 0.4 cm. Diameter, 1 mm. Color, 135B.
- *Pedicel.*—Length, 15 mm, Diameter, 1 mm. Color, 136B.
- *Fragrance.*—None.

Storage root:
- *Shape.*—Oval and rounded at the stem-end with a slight root protrusion at the distal tip of the root.
- *Length.*—15.2 cm (not including slight distal protrusion).
- *Width.*—7.1 cm.
- *Skin color.*—186C.
- *Flesh color.*—79C.

What is claimed is:

1. A new and distinct variety of *Ipomoea batatas* plant, substantially as herein described and illustrated.

* * * * *